United States Patent [19]

Kirsch et al.

[11] Patent Number: 5,492,452
[45] Date of Patent: Feb. 20, 1996

[54] FASTENING NAIL AND AN ASSEMBLY OF TOOLS FOR SECURING THE NAIL

[75] Inventors: Axel Kirsch, Sonnenbergstrasse 37, D70184 Stuttgart; Walter Duerr, Remchingen, both of Germany

[73] Assignees: Axel Kirsch, Filderstadt; Eberle Medizintechnische Elemente GmbH, Wurmberg, both of Germany

[21] Appl. No.: 175,967

[22] Filed: Dec. 30, 1993

[30] Foreign Application Priority Data

Jan. 4, 1993 [DE] Germany ............... 43 00 039.8

[51] Int. Cl.6 ............... F16B 15/06; F16B 15/08
[52] U.S. Cl. ............... 411/455; 411/456; 411/922; 606/67
[58] Field of Search ............... 411/455, 456, 411/484, 498, 922; 606/67, 75

[56] References Cited

U.S. PATENT DOCUMENTS

| | | | |
|---|---|---|---|
| 368,687 | 8/1887 | Rogers | 411/455 |
| 1,200,594 | 10/1916 | Curtis | 411/455 |
| 1,395,960 | 11/1921 | Hill | 411/484 |
| 1,490,722 | 4/1924 | Bacon | 411/455 |
| 3,325,135 | 6/1967 | Clarke | 411/455 X |
| 3,921,496 | 11/1975 | Helderman | 411/455 X |

Primary Examiner—Neill R. Wilson
Attorney, Agent, or Firm—Hill, Steadman & Simpson

[57] ABSTRACT

A fastening nail for fixing a cover membrane to a bone void which surrounds the bone of the body itself and is filled with an ossiferous material has a nail head with a larger diameter which enables receiving pressure of an impact tool for inserting a nail shaft with a smaller diameter into the bone. The nail shaft has essentially a cylindrical holding part extending to a conical tapering point part adjacent one end and is provided with a transition region between the holding part and point part having an annular shoulder with an enlarged diameter which has a conical surface merging obliquely with the generated surface of the point part in a direction toward the point of the nail and an annular surface extending substantially perpendicular relative to the holding axis of the nail. To insert the nail, the setting tool is elongated and has resilient jaws for gripping the nail and is used in combination with an auxiliary tool which has a foot with downwardly extending points for holding the membrane on the bone. The foot is provided with a setting opening which is large enough to allow inserting the nail through the opening to secure the membrane on the bone and the foot is provided with a drill template that is movable into the opening to position the drill when forming a pilot hole for the nail.

7 Claims, 2 Drawing Sheets

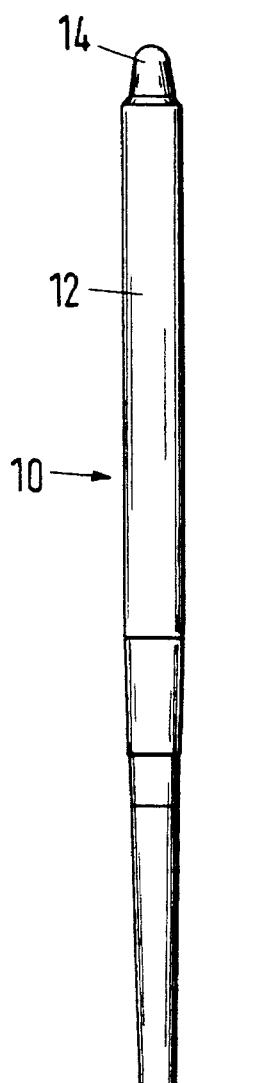
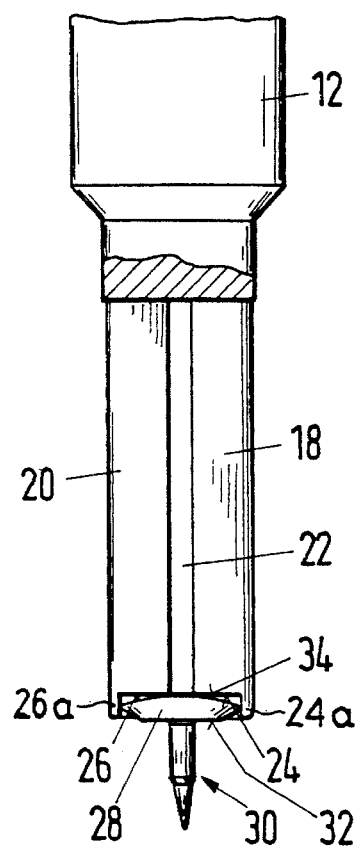
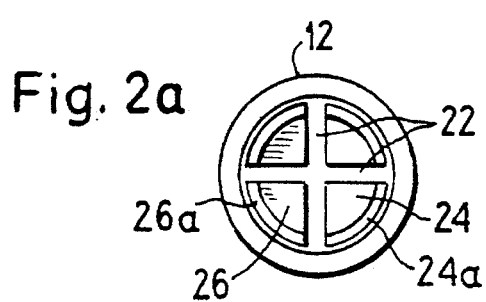
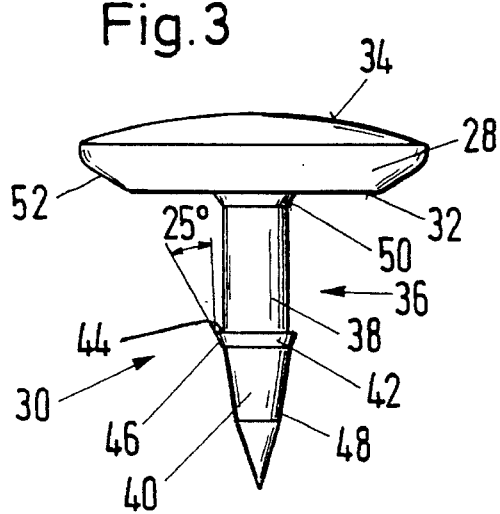

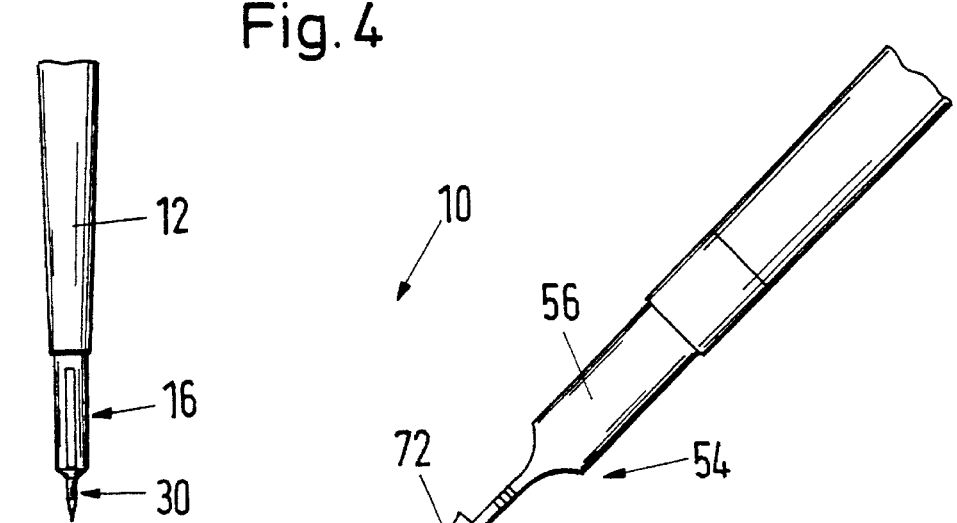
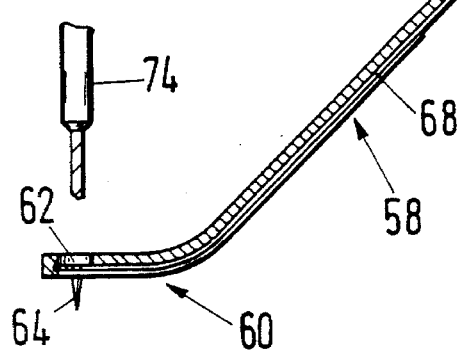
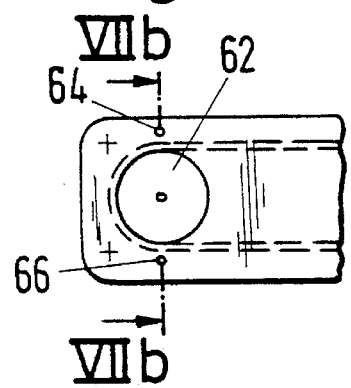
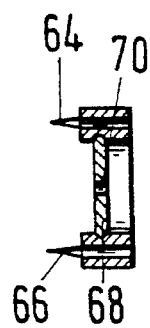
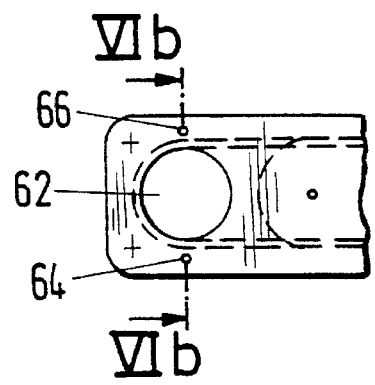
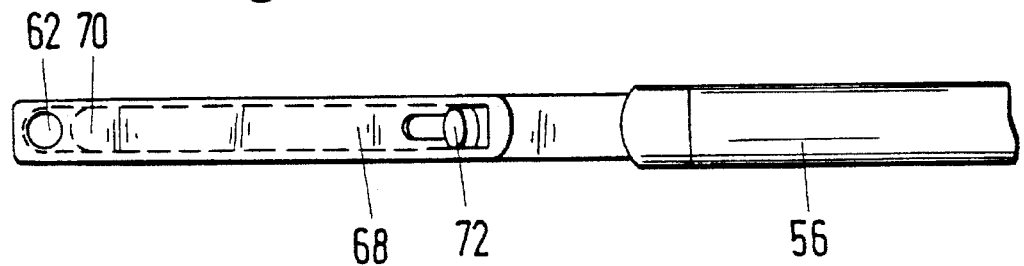

FASTENING NAIL AND AN ASSEMBLY OF TOOLS FOR SECURING THE NAIL

BACKGROUND OF THE INVENTION

The present invention is directed to a fastening nail for fixing a cover membrane to a bone void in a surrounding body-intrinsic bone filled with ossiferous material. The fastening nail has a nail head with a larger diameter enabling charging it with a pressure and/or an impact tool and having a nail shaft of a smaller diameter adjoining thereto, which comprises an essentially cylindrical holding part and an essentially conical tapering point end adjacent thereto. The invention is also directed to a setting tool for the insertion of the fastening nail.

In the field of maxillary surgery, it is standard to fill voids in the body-intrinsic bone with a bone replacement or ossiferous material which, for example, is composed of hydroxyl apatite granules, potentially mixed with bone granules of the body itself. A void filled with this ossiferous material is then covered with a cover membrane composed of a body-compatible plastic material or the like which will lie against the bone of the body itself next to the void. This is important so that the ossiferous material is penetrated in an osseous fashion by the bone of the body itself, whereby it is undesirable to have some other type of connective tissue, particularly mucous membrane tissue, growing through the ossiferous material, since a satisfactory filling of the bone void with the rejuvenated bone material does not occur in this case.

It has been difficult up to now to fix the cover membrane to the bone of the body itself reliably and tightly around the void so that one is able to avoid the undesirable growth of the non-osseous tissue into the bone void.

SUMMARY OF THE INVENTION

An object of the present invention is to create or provide a fastening nail plus a setting tool for the introduction of the nail with which it is possible to secure the cover membrane to the bone of the body itself or, respectively, to the solid bone of the body reliably and tightly in a simple manner so that an exclusive or at least nearly far-reaching in-growth of an ossiferous material with osseous tissue can be guaranteed.

In the improvement of the fastening nail, this objective is inventively achieved in that the transition region between the holding part and the point part comprises an annular shoulder having an enlarged diameter that, in the direction toward the point of the nail, has a conical surface merging obliquely into the generated conical surface of the point part and, in the direction toward the nail head, has an annular surface extending essentially perpendicular to the longitudinal axis of the fastening nail forming a barb-like element for the holding part.

It can, thus, be seen that the conical surface of the annular shoulder merges from the outer circumference of the annular surface into the generated surface of the point part without a significant change in the taper of the cone.

The invention also provides that the conical surface of the annular shoulder describes a larger angle with the longitudinal axis of the fastening nail than does the region of the generated conical surface forming the point adjacent thereto.

Another embodiment of the fastening nail of the invention is that the angle between the conical surface of the annular shoulder and the longitudinal axis of the fastening nail is approximately 25°.

The fastening nail can also be constructed so that the generated surface of the holder part has a beveled portion merging into the pressing surface of the nail head which proceeds essentially perpendicular relative to the longitudinal axis of the fastening nail.

It can also be provided in the invention that the nail head comprises a circumferential bevel at its circumferential edge adjoining the pressing surface which ascends from the latter in a direction to the head surface of the nail facing away from the nail shaft.

The invention further provides that the head surface of the nail is fashioned rounded in a proposed fastening nail. The nail is preferably made of a titanium alloy or the like which is employed as a manufacturing material.

The setting tool of the invention for inserting the claimed fastening nail is characterized by an elongated, pencil-like gripping part at whose one end is a pressure/impact head for receiving blows from a tool, such as a hammer, and the other end has resilient means for holding the fastening nail. The resilient means is provided with at least two resilient gripper jaws, and preferably four jaws, which are constructed or separated by crosswise-extending slots.

The invention further provides that the gripper jaws are constructed of one piece with the region of the surface of the gripping part adjacent thereto. The invention also proposes that the gripping jaws each, respectively, comprise a seating shoulder for the head surface of the fastening nail and spacing therefrom the end face of the holder means facing away from the gripping part being smaller than the height of the nail head.

Another embodiment is a combination of the setting tool with an auxiliary tool or a setting aid which is independent of the setting tool. The auxiliary tool has a gripping part, a fixing part adjacent thereto which comprises a retainer foot provided with a setting opening and engageable against the bone, and the diameter of the opening is slightly larger than the outside diameter of the holder means for the nail. The auxiliary tool also has a drill template of flexible sheet metal or the like that is displaceable into the section opening and has the drill opening at its end neighboring the setting opening and can be retracted from a drilling position or first position wherein the setting opening is closed except for the drill opening into a retracted position, wherein the setting opening is uncovered.

It can thereby be provided that the retainer foot comprises at least two acute retainer arbors or pin points on the underside that can be placed against the bone. These arbors or points are provided to lie diametrically opposite one another on both sides of the setting opening.

A further embodiment of the invention provides that the drilling template is slidably held in a track of the fixing part and is provided with an actuating element close to the gripping part, which actuating element is capable of being actuated by the operator without letting go of the gripping part.

The invention is based on the surprising perception that the previously-existing problems when covering voids filled with ossiferous material can be successfully solved in that the cover membrane is reliably fixed to the solid bone of the body with a fastening nail in the location of the void, and this will guarantee that the cover membrane is tightly pressed against the bone of the body itself as a consequence of the barb-like fashioning of the nail. When the preferred embodiment of the setting tool of the invention is employed with the auxiliary tool, the cover membrane can first be exactly and firmly fixed to the bone with the auxiliary tool given a lateral fixing due to the retaining arbors or points of the holding foot. After a pilot or guide bore has been provided in the bone material, which will lie exactly in the middle of the setting opening, a fastening nail can then be introduced into this pilot hole or guide bore exactly and without lateral dislocation through the setting opening with the setting tool after the drill template has been retracted so that the cover membrane is reliably and tightly fixed to the bone.

Other advantages and features of the invention will be readily apparent from the following description of the preferred embodiments, the drawings and claims.

BRIEF DESCRIPTION OF THE DRAWINGS

FIG. 1 is a side view of a setting tool of the present invention with an exemplary embodiment of the fastening nail of the invention;

FIG. 2 is an enlarged side view of the end of the setting tool of the present invention with portions broken away for purposes of illustration showing the holding of a fastening nail therein;

FIG. 2a is an end view of the tool of FIG. 2;

FIG. 3 is a side view of the fastening nail of FIGS. 1 and 2;

FIG. 4 is a side view of an auxiliary setting tool of the present invention with portions broken away for purposes of illustration;

FIG. 5 is a top plan view of the auxiliary setting tool of FIG. 4;

FIG. 6a is a partial end view of the retaining foot of the auxiliary setting tool with the drill template in the withdrawn position;

FIG. 6b is a cross sectional view taken along the lines VIb—VIb of FIG. 6a;

FIG. 7a is an enlarged end view similar to FIG. 6a of the foot of the auxiliary setting tool with the drill template in the engaged or drilling position; and FIG. 7b is a cross sectional view taken along the lines VIIb—VIIb of FIG. 7a.

DESCRIPTION OF THE PREFERRED EMBODIMENTS

The principles of the present invention are particularly useful in a setting tool, generally indicated at 10 in FIGS. 1 and 4, and to a fastening nail, generally indicated at 30 in FIGS. 1–3.

The setting tool 10 of the present invention comprises an elongated, pencil-like grip part 12 which has a pressure/impact head 14 provided at one end for receiving blows, for example from a hammer. At an opposite end, the tool 10 has resilient means 16 for holding a nail 30. As best illustrated in FIGS. 2 and 2a, the resilient means 16 comprises four gripping jaws 18 and 20, which are separated from one another by cross-extending slots 22 which are formed in the end of the tool 10. Each of the jaws 18 have a seating surface 24 and the jaws 20 have a seating surface 26, which is recessed so that each jaw 18 has an outer portion or lip 24a adjacent the surface 24 and the jaws 20 have a lip or portion 26a adjacent the surface 26. These portions 24a and 26a form a recess for receiving a head 28 of the nail 30 which has an upper convex surface 34 which is rounded and the height of the head 28 between a pressing surface 32 is greater than the depth of the recess formed by the portions 24a and 24b so that when a nail head is received, the surface 32 extends below the lower edges of the lips 24a and 26a.

As best shown in FIG. 3, the nail 30 includes a nail shaft, generally indicated at 36, which extends from the center of the head 28 and is composed of an essentially cylindrical holding part 38 that terminates in a point part 40. The nail is a single member and is provided with an annular shoulder 42 between the holding part 38 and the point part 40. The annular shoulder 42 has an annular surface 44 which extends essentially perpendicular relative to the longitudinal axis of the fastening nail and merges into a generated surface of the holding part 38. A conical surface 46 adjoins the annular surface 44 in the direction toward the point of the nail and the angle of this conical surface 46 with the longitudinal axis of the fastening nail amounts to approximately 25° in the illustrated exemplary embodiment. This angle is larger than that of the generated conical surface 48 of the point part 40 relative to the longitudinal axis of the fastening nail. The generated surface of the holding part 38 of the nail 30 merges into the pressing surface 32 of the nail head 28 with a bevel 50. A circumferential bevel 52 extends from the pressing surface 32 of the nail head 28 at a larger outside circumference thereof. Preferably, the entire nail is composed of a body-compatible titanium alloy.

As illustrated in FIG. 4, the setting tool can include an insertion aid or auxiliary tool, generally indicated at 54, which includes a handle portion 56 and a fixing part 58. The fixing part 58 comprises a retainer foot 60 that is provided with a setting opening 62 on whose two sides retainer arbors, pins or points 64, 66 are arranged to lie diametrically opposite one another. A drill template 68 composed of a flexible sheet has a drill opening 70 at its end facing away from the gripping part 56 and has an actuation element 72 on its end facing toward the gripping part. This template 68, thus, is built to slide in a groove provided in the part 58 from a drilling or first position illustrated, such as in FIG. 7a, to a retracted position, such as illustrated in FIG. 6a.

The present invention is utilized as follows. In the simplest case, when there is no prior introduction of a pilot hole or guide bore in the solid bone of the body itself is necessary, a fastening nail 30 may .be introduced into the resilient means 16 of the setting tool 10 in the form such as illustrated in FIG. 2. The gripping jaws 18 and 20 resiliently hold the nail head 28 so that the head surface 34 presses against the seating shoulders 24 and 26 of the gripping jaws 18 and 20. As a consequence of the dimensioning that was set forth above, the pressing surface 32 of the fastening nail lies below the end faces of the projections 24a and 26a and will engage the bone before these projections will. The gripping part 12 of the setting tool is grasped by the operator, whereupon the fastening nail is pressed into the bone or is driven into the bone given the assistance of a hammer striking the pressure/impact head 14. As a result of this, the cover membrane lying on the bone is firmly clamped between the pressing surface 32 of the nail head 28 and the bone surface adjacent thereto. The bevel 50 prevents undesirable mucous membrane residues or the like from collecting in a "dead angle". As a result of the tight placement of the cover membrane (not shown) against the bone, soft connective tissue, particularly mucous tissue, is prevented from penetrating and growing into the void of the bone covered with the cover membrane and filled with the bone replacement material. As a result, an osseous in-growth of the bone replacement or ossiferous compound is guaranteed. The seating shoulder 42, which is barb-like, thereby guarantees a firm seating or anchoring of the fastening nail 30 in the bone. The circumferential bevel 52 makes it possible to, in turn, remove the fastening nail 30 from the bone when desired by applying a forceps or the like.

In general, the bone of the body itself is too hard for the fastening nail 30 to be introduced without a prior introduction of a pilot hole or guide bore into the bone. One then proceeds as follows. Using the auxiliary tool 54 of FIGS. 4–7, the cover membrane is pressed against the bone, wherein the retaining pins or points 64, 66 will secure the membrane on the bone in a point-like fashion in a manner in which they will not be laterally dislocatable. The retainer foot 60 of the auxiliary tool 54 thereby presses flush against the bone or, respectively, against the covering membrane covering the bone. When the drilling template 68 is advanced to the drilling or first position, the setting opening 62 will be completely closed, except for the drill opening 70, as illustrated in FIGS. 7a and 7b. The formation of the guide bore of the pilot hole is accomplished with the drill 74 passing through the drill opening 70. The drill 74 is then withdrawn and the drill template 68 is retracted to the retracted position without the retainer foot 60 being lifted from the bone of the body itself, which is covered by the cover membrane. The fastening nail 30 is then introduced into the pilot hole through the setting opening 62, which is now uncovered, using the setting tool 10 which the operator holds at the gripping part 12 with his free hand. The diameter of the pilot hole or guide bore is preferably selected so that it roughly corresponds to the outside diameter of the holding part 38 of the fastening nail 30, but is smaller than the outside diameter of the annular shoulder 42 so that the shoulder 42 can exercise its barb-like retaining function.

Although various minor modifications may be suggested by those versed in the art, it should be understood that we wish to embody within the scope of the patent granted hereon all such modifications as reasonably and properly come within the scope of our contribution to the art.

We claim:

1. A fastening nail for securing a cover membrane to a bone void which surrounds the bone of a body itself, which void is filled with an ossiferous material, said nail comprising an essentially cylindrical holding part having an essentially conical tapering point part adjacent one end and a nail head with a pressing surface and a substantially larger diameter adjacent the opposite end, a transition region between the holding part and the point part having an annular shoulder with an enlarged diameter which has a conical surface merging obliquely into the generated surface of the conical tapering point part in a direction toward the point of the nail and has an annular surface extending essentially perpendicular to a longitudinal axis of the fastening nail adjoining the holding part to form an annular barb-like shoulder facing toward the nail head.

2. A fastening nail according to claim 1, wherein the conical surface of the annular shoulder describes a larger angle with the longitudinal axis of the fastening nail than the conical surface forming the point part adjacent thereto.

3. A fastening nail according to claim 2, wherein the angle between the conical surface of the annular shoulder and the longitudinal axis of the fastening nail amounts to approximately 25°.

4. A fastening nail according to claim 1, wherein the holding part has a bevel at a point of merger with the pressing surface of the nail head, which pressing surface extends essentially perpendicular relative to the longitudinal axis of the fastening nail.

5. A fastening nail according to claim 1, wherein the circumferential edge of the nail head has a circumferential bevel adjacent the pressing surface, which bevel ascends from the pressing surface in a direction toward the head surface of the nail head facing away from the nail shaft.

6. A fastening nail according to claim 1, wherein the head surface of the nail head is a rounded surface.

7. A fastening nail according to claim 1, wherein the nail is formed of a titanium alloy.

\* \* \* \* \*